US011045563B2

(12) United States Patent
Wouters et al.

(10) Patent No.: US 11,045,563 B2
(45) Date of Patent: *Jun. 29, 2021

(54) MONO-, DI- OR POLYSACCHARIDE USED AS METAL INHIBITOR IN THE PREPARATION OF 68GA-CHELATE-FUNCTIONALIZED TARGETING AGENT

(71) Applicant: ANMI S.A., Liège (BE)

(72) Inventors: Ludovic Wouters, Herve (BE); Geoffroy Kaisin, Seraing (BE); André Luxen, Ocquier-Clavier (BE); Marc Léonard, Flémalle (BE); Samuel Voccia, Liège (BE)

(73) Assignee: ANMI S.A., Liège (BE)

( * ) Notice: Subject to any disclaimer, the term of this patent is extended or adjusted under 35 U.S.C. 154(b) by 289 days.

This patent is subject to a terminal disclaimer.

(21) Appl. No.: 15/505,945

(22) PCT Filed: Jul. 28, 2015

(86) PCT No.: PCT/EP2015/067213
§ 371 (c)(1),
(2) Date: Feb. 23, 2017

(87) PCT Pub. No.: WO2016/030104
PCT Pub. Date: Mar. 3, 2016

(65) Prior Publication Data
US 2018/0230069 A1  Aug. 16, 2018

(30) Foreign Application Priority Data

Aug. 29, 2014  (BE) .................. 2014/0653

(51) Int. Cl.
*A61K 51/04* (2006.01)
*C07B 59/00* (2006.01)
(52) U.S. Cl.
CPC ........ *A61K 51/0482* (2013.01); *C07B 59/008* (2013.01); *C07B 2200/05* (2013.01)
(58) Field of Classification Search
None
See application file for complete search history.

(56) References Cited

U.S. PATENT DOCUMENTS

| 4,387,303 | A | 6/1983 | Benjamins |
| 7,230,085 | B2 | 6/2007 | Griffiths et al. |
| 8,007,766 | B2 | 8/2011 | Velikyan et al. |
| 2003/0176784 | A1 | 9/2003 | Griffiths et al. |
| 2006/0182687 | A1 | 8/2006 | Yang et al. |
| 2007/0269375 | A1 | 11/2007 | Chen et al. |
| 2012/0009124 | A1 | 1/2012 | Port et al. |
| 2012/0134920 | A1* | 5/2012 | D'Souza ............ A61K 51/0406 424/1.53 |
| 2013/0130537 | A1 | 5/2013 | Keswani |
| 2013/0310537 | A1 | 11/2013 | Mueller |
| 2014/0171637 | A1 | 6/2014 | Fungazza et al. |
| 2018/0230068 | A1 | 8/2018 | Wouters et al. |
| 2018/0267050 | A1 | 9/2018 | Wouters et al. |
| 2019/0361030 | A1 | 11/2019 | Wouters et al. |

FOREIGN PATENT DOCUMENTS

| JP | 2009-161549 A | 7/2009 |
| RU | 2333557 C2 | 9/2008 |
| WO | 03/059397 A2 | 7/2003 |
| WO | 2008119036 A2 | 10/2008 |
| WO | 2010/092114 A1 | 8/2010 |
| WO | 2010141833 A2 | 12/2010 |
| WO | 2013/024013 A2 | 2/2013 |
| WO | 2013024013 A2 | 2/2013 |
| WO | 2014066733 A2 | 5/2014 |
| WO | 2016/030103 A1 | 3/2016 |
| WO | 2016030104 A1 | 3/2016 |
| WO | 2017191604 A2 | 11/2017 |

OTHER PUBLICATIONS

Cerchiaro et al. Investigations of different carbohydrate anomers in copper(II) complexes with D-glucose, D-fructose, and D-galactose by Raman and EPR spectroscopy. 2005 Carbohydr. Res. 340: 2352-2359. (Year: 2005).*

Norkus E. Metal ion complexes with native cyclodextrins. An overview. 2009 J. Incl. Phenom. Macrocycl. Chem. 65: 237-248 (Year: 2009).*

Communication Pursuant to Article 94(3) EPC dated Nov. 20, 2018 in connection with European Patent Application No. 15748207.6, 8 pages.

Communication Pursuant to Article 94(3) EPC dated Nov. 20, 2018 in connection with European Patent Application No. 15748208.4, 7 pages.

Haubner, Roland et al: "Development of 68Ga-labelled DTPA galactosyl human serum albumin for liver function imaging", European Journal of Nuclear Medicine and Molecular Imaging, vol. 40, No. 8, Apr. 12, 2013, pp. 1245-1255.

Prinsen, Kristof et al: "Development and evaluation of a 68Ga labeled pamoic acid derivative for in vivo visualization of necrosis using positron emission tomography", Bioorganic & Medicinal Chemistry, vol. 18, No. 14, Jul. 15, 2010, pp. 5274-5281.

Koop, Bernd et al: "Labelling of a monoclonal antibody with 68Ga using three DTPA-based bifunctional ligands and their in vitro evaluation for application in radioimmunotherapy", Radiochimica Acta, vol. 95, No. 1, Jan. 1, 2007, pp. 39-42.

Prata, M. I. M. et al: "Targeting of lanthanide(III) chelates of DOTA-type glycoconjugates to the hepatic asyaloglycoprotein receptor: cell internalization and animal imaging studies", Contrast Media & Molecular Imaging, vol. 1, No. 6, Jan. 1, 2006, pp. 246-258.

(Continued)

*Primary Examiner* — Jennifer Lamberski
(74) *Attorney, Agent, or Firm* — Amster, Rothstein & Ebenstein LLP

(57) ABSTRACT

The present invention relates the use of metal inhibitor in radiolabelling reactions using radioactive metals.

11 Claims, No Drawings

(56) References Cited

OTHER PUBLICATIONS

PCT International Search Report and Written Opinion dated Nov. 13, 2015 for PCT International Patent Application No. PCT/EP2015/067213, 13 pages.

Search Report dated Jan. 26, 2015 for Belgian Patent Application No. 2014/0653, 13 pages.

Eppard E et al., entitled "Ethanol-Based Post-processing of Generator-Derived 68Ga Toward Kit-Type Preparation of 68GA-Radiopharmaceuticals," Journal of Nuclear Medicine, vol. 55, No. 6, Jun. 2014, pp. 1023-1028.

Choi J Y et al., entitled "Development of 68Ga-labeled mannosylated human serum albumin (MSA) as a lymph node imaging agent for positron emission tomography," Nuclear Medicine and Biology, vol. 38, No. 3, 2011, pp. 371-379.

Larenkov A. A. et al., "Gallium Radionuclides in Nuclear Medicine: Radiopharmaceuticals Based on 68Ga," Medical radiology and radiation safety, 2011, vol. 56, No. 5, 56-73.

Russian Search Report dated Dec. 19, 2018 in connection with Russian Application No. 2017109582.

Russian Office Action, dated Dec. 2018, in connection with Russian Application No. 2017109582.

Maus S et al., entitled "Aspects on radiolabeling of 177Lu-DOTA-TATE: After C18 purification re-addition of ascorbic acid is required to maintain radiochemical purity," International Journal of Diagnostic Imaging, 2014, vol. 1, No. 1, pp. 5-12.

Japanese Notification of Reasons for Refusal issued in Application No. 2017-530410, dated Feb. 5, 2019.

Office Action dated Nov. 8, 2019 from Russian Patent Application No. 2017109583.

Green et al., "Carbohydrate-Bearing 3-Hydroxy-4-pyridinonato Complexes of Gallium(III) and Indium(III)," Bioconjugate Chem., vol. 16, No. 6, 2005, pp. 1597-1609.

Rizzello et al., "Synthesis and Quality Control of 68GA Citrate for Routine Clinical PET," Nuclear Medicine Communications, vol. 30, No. 7, 2009, pp. 542-545.

Third Party Submission Under 37 CFR § 1.290 dated Mar. 18, 2019 in U.S. Appl. No. 15/981,951.

International Search Report and Written Opinion dated Nov. 12, 2015 in PCT International Appln. No. PCT/EP2015/067211.

Russian Office Action dated Nov. 8, 2019 in Russian Application No. 2017109582 with English language translation.

Mexican Office Action dated Oct. 27, 2020 from Mexican Patent Appln. No. MX/a/2017/002361 (with English language translation attached).

Leyva Ramos et al., "Agentes Quelantes Bifuncionales Utilizados en la Síntesis de Radiofármacos," Rev. Mex. Cienc. Farm., vol. 44, No. 1, Jan.-Mar. 2013, pp. 7-23 (with English language Abstract and concise explanation included in Office Action—see description of reference No. D5).

Australian Examination Report dated Dec. 2, 2019 for Australian Patent Appl. No. 2015309188.

Price E.W. and Orvig C. Matching chelators to radiometals for radiopharmaceuticals. Chemical Society Reviews, vol. 43, No. 1, Jan. 7, 2014, pp. 260-290.

\* cited by examiner

MONO-, DI- OR POLYSACCHARIDE USED AS METAL INHIBITOR IN THE PREPARATION OF 68GA-CHELATE-FUNCTIONALIZED TARGETING AGENT

CROSS-REFERENCE TO RELATED APPLICATIONS

This application is a U.S. national stage entry under 35 U.S.C. § 371 of PCT International Patent Application No. PCT/EP2015/067213, filed Jul. 28, 2015, which claims priority to Belgian Patent Application No. 2014/0653, filed Aug. 29, 2014, the contents of which are incorporated herein by reference in their entirety.

TECHNICAL FIELD

The present invention is related to metal inhibitor improving radiolabelling yields and reliability

BACKGROUND

Recently, some very interesting clinical results based on gallium-68 radiolabeled molecules for imaging in vivo by PET were published and presented. These radiopharmaceuticals are generally made of by assembly of a chelating agent with a targeting agent, generally DOTA-functionalized targeting agents, allowing, respectively, the reaction with a metallic radioisotope or radioactive metal and biological/metabolic activity of the radiopharmaceutical. This diagnostic isotope, i.e. gallium-68, has gained much interest because its substitution with lutecium-177 allows to switch from a diagnostic molecule to a therapeutic analogue readily usable for targeted radiotherapy. This "theranostic" (standing for diagnostic and therapeutic) field is in growth and will lead to major improvements in healthcare especially in oncology (J. Nucl. Med. 2011, 52, 841).

Among the radioactive metals usable for diagnostic or radiotherapy there is:
copper-64, gallium-68, gallium-67, gallium-66, lutecium-177, yttrium-86, yttrium-90, indium-114, indium-111, scandium-47, scandium-44, scandium-43, zirconium-89, bismuth-213, bismuth-212, actinium-225, lead-212, rhenium-188, rhenium-186, rubidium-82 and the like.

The labelling reaction with these radioactive metals is generally performed by chelating the radioactive metal with a suitable chelating agent in a suitable reaction medium, usually in a buffered medium in order to ensure an optimum pH for the chelation reaction.

However, these radioactive metals or their parent isotopes when issued from generators, are generally produced by cyclotron irradiation of either solid or liquid targets. Due to this production path these radioactive metals are generally not pure and contains some metallic byproducts.

The chelation reaction is dependent on a suitable pH, but on possible competition of the metallic impurities mentioned above with radioactive metals during the chelation reaction as well. In addition, it is generally accepted that heat can promotes the chelation reaction for the most commonly used radioactive metals based radiopharmaceuticals.

In the state of the art, the presence of metal ions that compete with radioactive metals is generally reduced by pre-labelling purification or fractionation of the radioactive but these additional steps represent a loss of radioactivity resulting from, either wasted time or the process itself. These losses can reach up to 30% of the total radioactivity.

The possibility of partial chelation of of the radioactive metal requires, in general, a final post-labelling purification which allows to obtain a radiopharmaceutical having a radiochemical purity meeting the pharmaceutical specifications (>90% radiochemical purity). These steps also represent an additional loss of activity that can raise up to 10% resulting from wasted time or the process itself.

According to known processes, at the end of the radiolabelling, a sequestering agent having a particular affinity for the unreacted radioactive metal may be added to chelate the non-reacted portion of the isotope. This complex formed by the sequestering agent and the non-reacted radioactive metal is then discarded in order to reach a better radiochemical purity after radiolabelling.

In addition, the need for these pre- and post-labelling purification steps makes these radioactive metal labelled radiopharmaceutical synthesis dependent, to some extent, on automation and on the use of a synthesis module. In addition to technical expertise, this requires extra time loss unfavorable to the overall performance.

Any improvement in order to achieve rapid, direct and high efficiency chelation is thus highly desirable.

Management of competing metal impurities is another challenge. Indeed, any species that would inhibit metal impurities by avoiding or having limited capacity to interfere negatively on the radioactive metal chelation reaction can act as a trap for these impurities. In other words, this inhibitory effect brings the apparent concentration of competitor metal, i.e. the concentration of metallic impurities yet available for chelation to a level which allows high yields and reproducible radiolabeling. This co-chelating agent is by definition different than the chelating agent assembled with the targeting agent.

In this context, it is clear that a need exists for an improved process for the preparation of radioactive metal complex which overcomes one or more of the above mentioned problems. This involves identifying an appropriate medium to handle the metal contamination, which if available avoids the need to heat for promoting the chelating reaction and allows radioactive metal chelation yields upper 90%. This heating is sometimes detrimental for the overall stability of the chelate-functionalized targeting agent

SUMMARY

The present invention is related to the use of metal inhibitors for improving radiolabelling yields and reliability of radioactive metal-based radiotracer synthesis, wherein the radiolabelling is performed with:
  A chelate-functionalized targeting agent, able to chelate the radioactive metal in the radiolabeling conditions
  A metal inhibitor, which is a co-chelating agent, capable of inactivating metals other than radioactive metal without interfering with the chelation between the radioactive metal and the said chelate-functionalized targeting agent, under the conditions of the labelling reaction. In other words, said metal inhibitor is selected for its ability to chelate contaminating metals interfering and competing with the chelation of the radioactive metal while being mostly unable to chelate the radioactive metal in the said conditions of the labelling reaction as opposed to the chelate-functionalized targeting agent;
  A radioactive metal; and
  Optionally a buffer The invention hence provides the following aspects:

Aspect 1. Use of a metal inhibitor for improving radiolabelling yields and reliability of radioactive metal-based radiotracer synthesis, wherein the radiolabelling is performed with:
- a chelate-functionalized targeting agent, able to chelate the radioactive metal in the radiolabeling conditions;
- a metal inhibitor, which is a co-chelating agent, capable of inactivating metals other than radioactive metal without interfering with the chelation between the radioactive metal and the said chelate-functionalized targeting agent, under the conditions of the labelling reaction;
- a radioactive metal; and optionally
- a buffer allowing to maintain the pH in the range 3-8

Aspect 2. The method according to aspect 1, wherein said targeting agent and metal inhibitor are present in a buffer consisting of phosphate, nitrate, HEPES, acetate, TRIS, ascorbate, or, citrate or a mixture thereof.

Aspect 3. The use according to aspect 1 or 2, wherein the radioactive metal is selected from the group comprising: copper-64, gallium-68, gallium-67, gallium-66, lutecium-177, yttrium-86, yttrium-90, indium-114, indium-111, scandium-47, scandium-44, scandium-43, zirconium-89, bismuth-213, bismuth-212, actinium-225, lead-212, rhenium-188, rhenium-186, and rubidium-82; or wherein the radioactive metal is not gallium-68.

Aspect 4. The use according to any one of aspects 1 to 3, wherein the radioactive metal is a metal linked to a radioactive species.

Aspect 5. The use according to any one of aspects 1 to 3, wherein the radioactive metal is a fluorine-18 based metal fluoride.

Aspect 6. The use according to any one of aspects 1 to 5, wherein the chelate functional group of the targeting agent is selected from the group comprising: DOTA and its derivatives, such as, DOTAGA, TRITA, DO3A-Nprop, BisDO3A and TrisDO3A; DTPA and its derivatives such as tetra-tBu-DTPA, p-SCN-Bz-DTPA, MX-DTPA and CHX-DTPA; NOTA and its derivatives, such as TACN, TACN-TM, DTAC, H3NOKA, NODASA, NODAGA, NOTP, NOTPME, PrP9, TRAP, Trappist Pr, NOPO, TETA; chelates open chain such as HBED, DFO, EDTA, 6SS, B6SS, PLED, TAME, YM103; NTP (PRHP) 3; the H2dedpa and its derivatives such as H2dedpa-1, 2-H2dedpa, H2dp-bb-NCS, and H2dp-N-NCS; (4,6-MeO2sal) 2-BAPEN; and citrate and derivatives thereof.

Aspect 7. The use according to any one of aspects 1 to 6, wherein said metal inhibitor is a sugar.

Aspect 8. The use according to any one of aspects 1 to 7, wherein said metal inhibitor is selected from the group comprising: monosaccharides and their derivatives, disaccharides and their derivatives, and polysaccharides and their derivatives and sulfated sugars.

Aspect 9. The use according to anyone of aspects 1 to 8, wherein said metal inhibitor is selected from the group comprising: Glucose, Fructose, Beta-cyclodextrin, D-Mannose, and Sulfated sugars.

Aspect 10. The use according to anyone of aspects 1 to 9, wherein said metal inhibitor and said functionalised agent are chemically linked.

Aspect 11. The use according to anyone of aspects 1 to 10, wherein said metal inhibitor and said functionalised agent are chemically linked, through a linker that is unstable in the radiolabelling conditions.

Aspect 12. The use according to anyone of aspects 1 to 11, wherein said radiolabelling is carried out at a temperature near or equal to room temperature.

Aspect 13. A method for radiolabelling a chelate-functionalized targeting agent with a metal radionuclide, comprising the steps of:
a) providing a chelate-functionalized targeting agent, able to chelate the radioactive metal in the radiolabeling conditions;
b) adding a metal inhibitor to said targeting agent of a), said metal inhibitor being a co-chelating agent, capable of inactivating metals other than radioactive metal without interfering with the chelation between the radioactive metal and the said chelate-functionalized targeting agent, under the conditions of the labelling reaction; and
c) adding a radioactive metal to the mixture of a) and b).

Aspect 14. The method according to aspect 13, wherein said targeting agent and metal inhibitor are present in a buffer allowing to maintain the pH in the range 3-8

Aspect 15. The method according to aspect 13 or 14, wherein said targeting agent and metal inhibitor are present in a buffer consisting of phosphate, nitrate, HEPES, acetate, TRIS, ascorbate, citrate or a mixture thereof.

Aspect 16. The method according to any one of aspects 13 to 15, wherein the radiolabeling reaction is carried out at a temperature of below 50° C., preferably of ambient or room temperature (e.g. of between 20 and 30° C.).

Aspect 17. The method according to any one of aspects 13 to 16, wherein the radiolabelling is performed at a pH comprised between 3 and 8, preferably between 3,5 and 7,5, more preferably between 3,5 and 7.

Aspect 18. The method according to any one of aspects 13 to 17, wherein the radioactive metal is selected from the group comprising: copper-64, gallium-68, gallium-67, gallium-66, lutecium-177, yttrium-86, yttrium-90, indium-114, indium-111, scandium-47, scandium-44, scandium-43, zirconium-89, bismuth-213, bismuth-212, actinium-225, lead-212, rhenium-188, rhenium-186, and rubidium-82; or wherein the radioactive metal is not gallium-68.

Aspect 19. The method according to any one of aspects 13 to 18, wherein the radioactive metal is a metal linked to a radioactive species.

Aspect 20. The method according to any one of aspects 13 to 18, wherein the radioactive metal is a fluorine-18 based metal fluoride.

Aspect 21. The method according to any one of aspects 13 to 20, wherein the chelate functional group of the targeting agent is selected from the group comprising: DOTA and its derivatives, such as, DOTAGA, TRITA, DO3A-Nprop, BisDO3A and TrisDO3A; DTPA and its derivatives such as tetra-tBu-DTPA, p-SCN-Bz-DTPA, MX-DTPA and CHX-DTPA; NOTA and its derivatives, such as TACN, TACN-TM, DTAC, H3NOKA, NODASA, NODAGA, NOTP, NOTPME, PrP9, TRAP, Trappist Pr, NOPO, TETA; chelates open chain such as HBED, DFO, EDTA, 6SS, B6SS, PLED, TAME, YM103; NTP (PRHP) 3; the H2dedpa and its derivatives such as H2dedpa-1, 2-H2dedpa, H2dp-bb-NCS, and H2dp-N-NCS; (4,6-MeO2sal) 2-BAPEN; and citrate and derivatives thereof.

Aspect 22. The method according to any one of aspects 13 to 21, wherein said metal inhibitor is a sugar.

Aspect 23. The method according to anyone of aspects 13 to 22, wherein said metal inhibitor is selected from the group comprising: monosaccharides and their derivatives, disaccharides and their derivatives, and polysaccharides and their derivatives and sulfated sugars.

Aspect 24. The method according to anyone of aspects 13 to 23, wherein said metal inhibitor is selected from the group comprising: Glucose, Fructose, Beta-cyclodextrin, D-Mannose, and sulfated sugars.

Aspect 25. The method according to any one of aspects 13 to 24, wherein said metal inhibitor and said functionalised agent are chemically linked.

Aspect 26. The method according to any one of aspects 13 to 25, wherein said metal inhibitor and said functionalised agent are chemically linked, through a linker that is unstable in the radiolabelling conditions.

Aspect 27. A radiolabelled chelate-functionalized targeting agent obtained by the method according to anyone of aspects 13 to 26.

Aspect 28. A radiolabelling kit comprising:
- a chelate-functionalized targeting agent, able to chelate the radioactive metal in the radiolabeling conditions;
- a metal inhibitor, which is a co-chelating agent, capable of inactivating metals other than radioactive metal without interfering with the chelation between the radioactive metal and the said chelate-functionalized targeting agent, under the conditions of the labelling reaction;
- a radioactive metal; and optionally
- a buffer. allowing to maintain the pH in the range 3-8

Aspect 29. The kit according to aspect 28, wherein said targeting agent and metal inhibitor are present in a buffer consisting of phosphate, nitrate, HEPES, acetate, TRIS, ascorbate, citrate or a mixture thereof.

Aspect 30. The kit according to aspect 28 or 29, wherein the radioactive metal is selected from the group comprising: copper-64, gallium-68, gallium-67, gallium-66, lutecium-177, yttrium-86, yttrium-90, indium-114, indium-111, scandium-47, scandium-44, scandium-43, zirconium-89, bismuth-213, bismuth-212, actinium-225, lead-212, rhenium-188, rhenium-186, and rubidium-82; or wherein the radioactive metal is not gallium-68.

Aspect 31. The kit according to any one of aspects 28 to 30, wherein the radioactive metal is a metal linked to a radioactive species.

Aspect 32. The kit according to any one of aspects 28 to 31, wherein the radioactive metal is a fluorine-18 based metal fluoride.

Aspect 33. The kit according to any one of aspects 28 to 32, wherein the chelate functional group of the targeting agent is selected from the group comprising: DOTA and its derivatives, such as, DOTAGA, TRITA, DO3A-Nprop, BisDO3A and TrisDO3A; DTPA and its derivatives such as tetra-tBu-DTPA, p-SCN-Bz-DTPA, MX-DTPA and CHX-DTPA; NOTA and its derivatives, such as TACN, TACN-TM, DTAC, H3NOKA, NODASA, NODAGA, NOTP, NOTPME, PrP9, TRAP, Trappist Pr, NOPO, TETA; chelates open chain such as HBED, DFO, EDTA, 6SS, B6SS, PLED, TAME, YM103; NTP (PRHP) 3; the H2dedpa and its derivatives such as H2dedpa-1, 2-H2dedpa, H2dp-bb-NCS, and H2dp-N-NCS; (4,6-MeO2sal) 2-BAPEN; and citrate and derivatives thereof.

Aspect 34. The kit according to any one of aspects 28 to 33, wherein said metal inhibitor is a sugar.

Aspect 35. The use according to anyone of aspects 28 to 34, wherein said metal inhibitor is selected from the group comprising: monosaccharides and their derivatives, disaccharides and their derivatives, and polysaccharides and their derivatives and sulfated sugars.

Aspect 36. The use according to anyone of aspects 28 to 35, wherein said metal inhibitor is selected from the group comprising: Glucose, Fructose, Beta-cyclodextrin, D-Mannose, and sulfated sugars.

Aspect 37. The kit according to any one of aspects 28 to 36, wherein said metal inhibitor and said functionalised agent are chemically linked.

Aspect 38. The kit according to any one of aspects 28 to 37, wherein said metal inhibitor and said functionalised agent are chemically linked, through a linker that is unstable in the radiolabelling conditions.

Aspect 39. The kit according to any one of aspects 28 to 38, wherein said chelate-functionalized targeting agent and metal inhibitor are lyophilised.

DETAILED DESCRIPTION

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms also encompass "consisting of" and "consisting essentially of".

The recitation of numerical ranges by endpoints includes all numbers and fractions subsumed within the respective ranges, as well as the recited endpoints.

The term "about" as used herein when referring to a measurable value such as a parameter, an amount, a temporal duration, and the like, is meant to encompass variations of and from the specified value, in particular variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" refers is itself also specifically, and preferably, disclosed.

Whereas the term "one or more", such as one or more members of a group of members, is clear per se, by means of further exemplification, the term encompasses inter alia a reference to any one of said members, or to any two or more of said members, such as, e.g., any $\geq 3$, $\geq 4$, $\geq 5$, $\geq 6$ or $\geq 7$ etc. of said members, and up to all said members.

All documents cited in the present specification are hereby incorporated by reference in their entirety.

Unless otherwise specified, all terms used in disclosing the invention, including technical and scientific terms, have the meaning as commonly understood by one of ordinary skill in the art to which this invention belongs. By means of further guidance, term definitions may be included to better appreciate the teaching of the present invention.

In the following passages, different aspects or embodiments of the invention are defined in more detail. Every aspect or embodiment so defined may be combined with each of the other aspects or embodiments unless stated otherwise. In particular, any feature indicated as being preferred or advantageous in one embodiment may be combined with any other embodiment or embodiments indicated as being preferred or advantageous.

The present invention overcomes one or more of the problems identified and observed in the state of the art and allows the direct radiolabeling of a chelate-functionalized targeting agents with radioactive metal.

The present invention is related to the use of a metal inhibitor for improving radiolabelling yields and reliability of radioactive metal-based radiotracer synthesis, the radiolabelling being performed with:
A chelate-functionalized targeting agent, able to chelate the radioactive metal in the radiolabeling conditions;

A metal inhibitor, which is a co-chelating agent, capable of inactivating metals other than radioactive metal without interfering with the chelation between the radioactive metal and the said chelate-functionalized targeting agent, under the conditions of the labelling reaction. In other words, said metal inhibitor is selected for its ability to chelate contaminating metals interfering and competing with the chelation of the radioactive metal while being mostly unable to chelate the radioactive metal in the said conditions of the labelling reaction as opposed to the chelate-functionalized targeting agent;

A radioactive metal; and

Optionally a buffer.

Furthermore, the present inventors have found that a metal inhibitor can be used in the radiolabeling method for neutralizing, at least partially, interfering species and allowing the radioactive metal to react with the chelate-functionalized targeting agent. These metal inhibitors may temporarily or permanently remove metals that compete with radioactive metal for the reaction with the chelate-functionalized targeting agent. Said metal inhibitor is thus unable to chelate the radioactive metal in the said conditions of the labelling reaction, but chelates other metals interfering with the chelation of radioactive metal by the chelate-functionalized targeting agent. The presence of metal inhibitors during the radiolabeling reaction provides an advantageous alternative to current approaches for managing the presence of metallic impurities such as increasing the amount of chelate-functionalized targeting agent or the pre-treatment of the eluate of the generator, these additional purification steps consume time (and radioactivity).

The aspects as described herein advantageously allow to obtain an appropriate chelation yield, particularly above 90%, and therefore a sufficient radiochemical purity without any preliminary or further final purification.

The presence of a chelate-functionalized targeting agent, optionally a buffer and a metal inhibitor in the labelling medium advantageously allows to directly transfer the radioactive metal to the targeting agent and to perform the radiolabeling reaction without the need for any prior or subsequent operation or purification.

In addition, all kit components as described herein can be lyophilized altogether or frozen which ensures a longer shelf life.

Thus, the main advantages of the invention as disclosed herein that differentiate from the state of the art are:

The possibility of radiolabeling without the need for an automated synthesizer;

The possibility of a radiolabelling without the need for heating;

The presence of a metal inhibitor which advantageously allows to use less chelate-functionalized targeting agent and allowing the implementation of more affordable radiopharmaceutical synthesis; and The presence of a metal inhibitor which advantageously allows improving the radiolabelling yields.

Metal inhibitors used in the present invention are selected for their ability to block the competing metals in the radiolabelling reaction without inhibiting the radioactive metal ions in their chelation reaction with the chelate-functionalized targeting agent. Indeed, these metal inhibitors should not interfere negatively on the main radiolabeling reaction or lead to the formation of secondary radiolabeled species. In other words metal inhibitors should have a limited or no capacity to complex radioactive metal in the conditions used for the radiolabelling reaction. Limited means at least 100 times less then the chelating agent used for the radiolabelling of the chelate-functionalized targeting agent.

It is interesting to note that the function of metal inhibitors in the present invention is the opposite of the function of the sequestering agents used in the prior art. Indeed, according to known methods, at the end of the labelling reaction, a sequestering agent having a particular affinity for e.g. the radioactive gallium may be added to chelate the unreacted portion of the isotope, whereas, according to the present invention an agent capable of reducing the competition of metallic impurities other than the radioactive metal is added at the beginning of the reaction.

As used herein, an "inhibitor of metal" refers to any molecule capable of interacting with, or competing metals, or the chelating moiety of the chelate-functionalized targeting agent or with radioactive metal directly, to inhibit wholly or partially the chelation the chelate-functionalized targeting agent said competing metals and/or promote the chelating of radioactive metal by said targeting agent.

Metal inhibitiors are preferably selected from the group of sugars. Sugars used as agents metal inhibitors in the kit of the invention can be monosaccharides or derivatives of monosaccharides such as tetracetose, pentacetose, hexacetose, tetrose, pentose, hexose, D-mannose, D-fructose, and derivatives; and/or disaccharides and their derivatives such as maltose and its derivatives; and/or polysaccharides and their derivatives such as dextrins, cyclodextrins, sulfated sugars, cellulose and derivatives thereof.

Preferably, the metal inhibitor is present in the kit as described herein in micromolar amounts, preferably in nanomolar quantities, preferably in an amount of less than 500 nanomolar, still more preferably in an amount less than 100 nanomoles.

The metal inhibitory agent may also be chemically bound to the chelate-functionalized targeting agent. This chemical bond can or cannot be a labile bond under the conditions of radiolabeling with the chelate-functionalized targeting agent like manner as in the conditions of radiolabeling the metal inhibitor is formed and released in situ.

As used herein, a "chelate-functionalized targeting agent" refers to a targeting agent capable of being labelled with a radioisotope such as for example radioactive metal, by means of an chelation agent to which this targeting agent is bound.

Preferred chelation agents for functionalizing a targeting agent to be radiolabeled with radioactive metals are those which form stable complexes at least for a time sufficient for diagnostic investigations using radiolabelled targeting agents. Suitable chelating agents include aliphatic amines, linear or macrocyclic such as macrocyclic amines with tertiary amines. While these examples of suitable chelating agents are not limited, they preferably include the DOTA and its derivatives, such as, DOTAGA, TRITA, DO3A-Nprop, BisDO3A and TrisDO3A; DTPA and its derivatives such as tetra-tBu-DTPA, p-SCN-Bz-DTPA, MX-DTPA and CHX-DTPA; NOTA and its derivatives, such as TACN, TACN-TM, DTAC, H3NOKA, NODASA, NODAGA, NOTP, NOTPME, PrP9, TRAP, Trappist Pr, NOPO, TETA; chelates open chain such as HBED, DFO, EDTA, 6SS, B6SS, PLED, TAME, YM103; NTP (PRHP) 3; the H2dedpa and its derivatives such as H2dedpa-1, 2-H2dedpa, H2dp-bb-NCS, and H2dp-N-NCS; (4,6-MeO2sal) 2-BAPEN; and citrate and derivatives thereof.

The chelate-functionalized targeting agent can be a peptide, for example, a peptide comprising 2 to 20 amino acids, a polypeptide, a protein, a vitamin, a saccharide, for example a monosaccharide or a polysaccharide, an antibody, nucleic acid, an aptamer, an antisense oligonucleotide, or an organic molecule.

Chelate-functionalized targeting agent as described herein preferably have a capacity of biological targeting. Non-limiting examples of suitable targeting agents include molecules that target VEGF receptors, analogs of bombesin or GRP receptor targeting molecules, molecules targeting somatostatin receptors, RGD peptides or molecules targeting αvβ3 and αvβ5, annexin V or molecules targeting the apoptotic process, molecules targeting estrogen receptors, biomolecules targeting the plaque . . . . More generally, a list targeting molecules, organic or not, functionalized by a chelating can be found in the journal of Velikyan et al., Theranostic 2014, Vol. 4, Issue 1 "Prospective of 68Ga-Radiopharmaceutical Development."

EXAMPLES

Example 1: Ga-68 Generator E & Z/NODAGA Peptide without Metal Inhibitor

Labelling a Peptide with a 68Ga Eluate of 5 mL of 0.1 M HCl

A solution of 1850 MBGa-68 of 6 (Eckert & Ziegler) is eluted with 5 mL of 0.1M HCl (Ultrapure grade) directly into a flask containing 150 mg of sodium acetate (Ultrapure grade) lyophilized, 240 µl of HCl 3M (Ultrapure grade), 760 µl of Milli-Q and 50 µg lyophilized NODAGA-NOC. The flask was left for 10 min at room temperature. The product is obtained with a radiochemical purity of 64% according to TLC analysis of the reaction medium.

Similarly to what was done in Example 1 different combinations were tested and are summarized in the table below:

| # | Radioactive metal | Chelating agent use in the chelate-functionalized targeting agent | Metal Inhibitor | Labelling conditions | Radiolabelling yield vs radiolabelling yield without inhibitor |
|---|---|---|---|---|---|
| 1 | Cu-64 | DOTA 25 µg | Glucose | 10 minutes, 65° C. | 82% vs 51% |
| 2 | Ga-68 | NODAGA 25 µg | Fructose | 10 min, R.T. | 97% vs 61% |
| 3 | Ga68 | NOTA 25 µg | Beta-cyclodextrin | 10 minutes, RT | 83% vs 51% |
| 4 | Sc-47 | DOTA 85 µg | Beta-cyclodextrin | 30 minutes, 60° C. | 85% vs 64% |
| 5 | Zr-89 | DFO | Beta-cyclodextrin | 30 minutes, RT | 91% vs 77% |
| 6 | Lu-177 | DOTA 100 µg | Fructose | 30 minutes, 65° C. | 94% vs 77% |
| 7 | In-111 | DOTA 100 µg | Fructose | 30 minutes, 65° C. | 85% vs 39% |
| 9 | Lu-177 | NODAGA 85 µg | Beta-cyclodextrin | 30 minutes, 40° C. | 95% vs 55% |
| 9 | Lu-177 | DOTA 100 µg | Beta-cyclodextrin | 30 minutes, 40° C. | 87% vs 51% |
| 10 | Ga-68 | NODAGA 25 µg | D-Mannose | 10 minutes, RT | 97% vs 76% |
| 11 | Ga-68 | DOTA 100 µg | D-Mannose | 30 minutes, RT | 80% vs 15% |
| 12 | Ga-68 | NODAGA 25 µg | Fucoidan | 10 minutes, RT | 93% vs 76% |

The term "radioactive metal" as used herein for radioactive labelling of the functionalised targeting agent(s) encompasses all radioactive metal ions suitable for use in medical imaging or radionuclides therapy. The radioactive metals are typically radioisotopes or radionuclides such as: copper-64, gallium-68, gallium-67, gallium-66, lutecium-177, yttrium-86, yttrium-90, indium-114, indium-111, scandium-47, scandium-44, scandium-43, zirconium-89, bismuth-213, bismuth-212, actinium-225, lead-212, rhenium-188, rhenium-186, rubidium-82 and the like. Many of these radionuclides are issued from nuclear reactor sub-products, cyclotron or from their specific radionuclide generator. In one embodiment, the radioactive metal is not gallium-68.

The term "radioactive metal" as used herein for radioactive labelling of the functionalised targeting agent(s) also encompasses metal linked to a radioactive species such as for example Fluorine-18-based metallic fluorides.

After addition of the radioactive metal solution to the metal inhibitor and the chelate-functionalized targeting agent, optionally containing a buffer, the solution obtained is left to the radiolabeling reaction for a short period of time, in particular between about 2 minutes and about 60 minutes, preferably from about 2 minutes to about 30 minutes, for example about 15 minutes.

The invention also discloses a radiolabeled targeting agent with radioactive metal, obtained by a method as described herein.

Said targeting agent and metal inhibitor were present in a buffer consisting of phosphate, nitrate, HEPES, acetate, TRIS, ascorbate, or citrate, or a mixture thereof.

The invention claimed is:
1. A method for radiolabelling a chelate-functionalized targeting agent with a metal radionuclide, comprising the steps of:
   a) providing a chelate-functionalized targeting agent, able to chelate the metal radionuclide in a radiolabelling reaction, wherein the chelate functional group of the chelate-functionalized targeting agent is selected from the group consisting of DOTA, NOTA, NODAGA, HBED, DFO, EDTA, 6SS, B6SS, PLED, TAME, YM103 and $H_2$dedpa;
   b) adding a metal inhibitor not chemically linked to said chelate-functionalized targeting agent, to the radiolabelling reaction obtained in a), said metal inhibitor being a co-chelating agent selected from the group consisting of beta-cyclodextrin and a monosaccharide, capable of inactivating metals other than metal radionuclides without interfering with the chelation between the metal radionuclide and the chelate-functionalized targeting agent, under the conditions of the radiolabelling reaction, thereby obtaining a mixture of the chelate-functionalized targeting agent of a) and the metal inhibitor of b) which are not chemically linked to each other when present in said mixture; and c) adding a metal radionuclide that is an isotope of a metal selected from the group consisting of copper, gallium, lutetium, indium, scandium, and zirconium to the mixture of a) and b) in an acetate buffer allowing to maintain the pH in the range 3-7, wherein the targeting agent of said chelate-functionalized targeting agent is selected from the group consisting of a peptide, a peptide comprising 2 to 20 amino acids, a polypeptide, an antibody, a nanobody, a diabody, an antibody fragment, a nucleic acid, an aptamer, an antisense oligonucleotide, and an organic molecule.

2. The method according to claim 1, wherein said metal inhibitor is present in micromolar amounts.

3. The method according to claim 1, wherein the radiolabelling reaction is carried out at a temperature of below 50° C.

4. The method according to claim 1, wherein the radiolabelling reaction is performed at a pH between 3 and 7.

5. The method according to claim 1, wherein the metal radionuclide is selected from the group consisting of copper-64, gallium-68, gallium-67, gallium-66, lutetium-177, indium-114, indium-111, scandium-47, scandium-44, scandium-43, and zirconium-89.

6. The method according to claim 1, wherein the monosaccharide is selected from the group consisting of Glucose, Fructose, and D-Mannose.

7. A radiolabelling kit comprising:

a chelate-functionalized targeting agent, able to chelate a metal radionuclide in a radiolabelling reaction, wherein the chelate-functional group of the chelate-functionalized targeting agent is selected from the group consisting of DOTA, NOTA, NODAGA, HBED, DFO, EDTA, 6SS, B6SS, PLED, TAME, YM103 and H$_2$dedpa;

a metal inhibitor, which is not chemically linked to said chelate-functionalized targeting agent and which is co-chelating agent selected from the group consisting of beta-cyclodextrin and a monosaccharide, capable of inactivating metals other than metal radionuclides without interfering with the chelation between the metal radionuclide and the chelate-functionalized targeting agent, under the conditions of the radiolabelling reaction;

a metal radionuclide that is an isotope of a metal selected from the group consisting of copper, gallium, lutetium, indium, scandium, and zirconium; and an acetate buffer, allowing to maintain the pH in the range 3-7, wherein the targeting agent of said chelate-functionalized targeting agent is selected from the group consisting of a peptide, a peptide comprising 2 to 20 amino acids, a polypeptide, an antibody, a nanobody, a diabody, an antibody fragment, a nucleic acid, an aptamer, an antisense oligonucleotide, and an organic molecule.

8. The kit according to claim 7, wherein said metal inhibitor is present in micromolar amounts.

9. The kit according to claim 7, wherein the metal radionuclide is selected from the group consisting of copper-64, gallium-68, gallium-67, gallium-66, lutetium-177, indium-114, indium-111, scandium-47, scandium-44, scandium-43, and zirconium-89.

10. The kit according to claim 7, wherein the monosaccharide is selected from the group consisting of Glucose, Fructose, and D-Mannose.

11. The kit according to claim 7, wherein said chelate-functionalized targeting agent and metal inhibitor are lyophilised.

* * * * *